United States Patent [19]

Schlaemus et al.

[11] Patent Number: 5,348,803
[45] Date of Patent: Sep. 20, 1994

[54] MICROCAPSULES AND METHOD FOR DEGRADING HYDROCARBONS

[75] Inventors: Herman W. Schlaemus; Mary C. Marshall; Michael G. MacNaughton; Matthew L. Alexander; James R. Scott, all of San Antonio, Tex.

[73] Assignee: Southwest Research Institute, San Antonio, Tex.

[21] Appl. No.: 744,093

[22] Filed: Aug. 12, 1991

[51] Int. Cl.$^5$ ................ B01J 13/02; C12N 11/02; C02F 3/00
[52] U.S. Cl. .................. 428/402.2; 210/610; 210/611; 210/922; 435/281; 435/177; 428/402.24
[58] Field of Search .......... 428/402.2, 402.24; 435/262, 281, 264, 178, 177; 210/922, 926, 610, 611

[56] References Cited

U.S. PATENT DOCUMENTS

| | | | |
|---|---|---|---|
| 3,843,517 | 10/1974 | McKinney et al. | 435/281 |
| 3,883,397 | 5/1975 | Townsley | 210/610 |
| 3,900,421 | 8/1975 | Fusey | 252/312 |
| 3,959,127 | 5/1976 | Bartha | 210/610 |
| 4,136,024 | 1/1979 | Bisa | 210/610 |
| 4,259,444 | 3/1981 | Chakrabarty | 435/281 X |
| 4,414,333 | 11/1983 | Olivieri et al. | 435/281 X |
| 4,415,661 | 11/1983 | Thirumalachar et al. | 435/281 X |
| 4,521,515 | 6/1985 | Hata | 435/264 X |

FOREIGN PATENT DOCUMENTS

| | | | |
|---|---|---|---|
| 2536087 | 5/1984 | France | 435/177 |
| 2600673 | 12/1987 | France | 435/178 |
| 204091 | 9/1986 | Japan | 435/177 |

*Primary Examiner*—Robert L. Stoll
*Assistant Examiner*—John M. Covert
*Attorney, Agent, or Firm*—John L. Sigalos

[57] ABSTRACT

A microcapsule for use in degrading a hydrocarbon comprising a core material, a coating material, and at least one microorganism capable of degrading said hydrocarbon, said core material comprising a lipophilic material containing nutrients necessary for the sustenance of said microorganism, said coating material being water-insoluble, and said capsule having a density such that said microcapsule is kept in close proximity to said hydrocarbon to be degraded whens said microcapsule is applied thereto; and the method of using the microcapsule to degrade hydrocarbons.

11 Claims, 1 Drawing Sheet

MICROCAPSULES AND METHOD FOR DEGRADING HYDROCARBONS

BACKGROUND OF THE INVENTION

The present invention relates to microcapsules for use in degrading hydrocarbons and the method for degrading hydrocarbons.

The use of microorganisms and, particularly bacteria, for degrading hydrocarbons is well known and efforts have been made over the past several years to utilize the same, particularly in combating the disastrous effects of oil spills on oceans, lakes, bays, rivers, and the like. Microorganisms which have been genetically engineered, particularly those containing plasmids providing a hydrocarbon degradative pathway have been applied to spills in an effort to degrade the same to prevent damage to the ecological systems in the area of the spill and avoid the loss of fish, plants, and mammals. Most commonly the microorganisms having the hydrocarbon degradation capability are applied as a slurry such as by being sprayed as an aqueous dispersion onto the oil spill. It will be evident that in such circumstances the microorganisms are exposed to the environment and many are not capable of surviving or being effective under the conditions of the particular environment in which the spill has occurred. The sunlight and ultraviolet light has a bactericidal effect on the organisms and there are insufficient levels of all required nutrients present to sustain the viability and growth of the organisms. As a consequence, while generally satisfactory in a laboratory environment to degrade hydrocarbons such as oils, they are ineffective in the real world environment where such spills take place.

As noted, one of the reasons for the lack of effectiveness is their inability to survive simply in the environment of the oil, whether it be spilled on land or on water. As a consequence the use of microorganisms having hydrocarbon degradative activity has not been as successful as originally thought in combating oil spills or other situations where it is desired to remove hydrocarbons that have contaminated either water areas such as bays, rivers, streams, oceans or land areas.

SUMMARY OF THE INVENTION

The present invention overcomes the problems of the prior art and provides microcapsules and a method capable of degrading a hydrocarbon effectively and efficiently.

Briefly stated, the present invention comprises a microcapsule for use in degrading a hydrocarbon comprising a core material, a coating material, and at least one microorganism capable of degrading said hydrocarbon, said core material comprising lipophilic material containing nutrients necessary for the sustenance of said at least one microorganism, said coating material being water-insoluble and said microcapsule having a density such that said microcapsule is kept in close proximity to said hydrocarbon.

The invention also comprises the method of degrading a hydrocarbon as set forth herein below.

DETAILED DESCRIPTION

Figure 1:
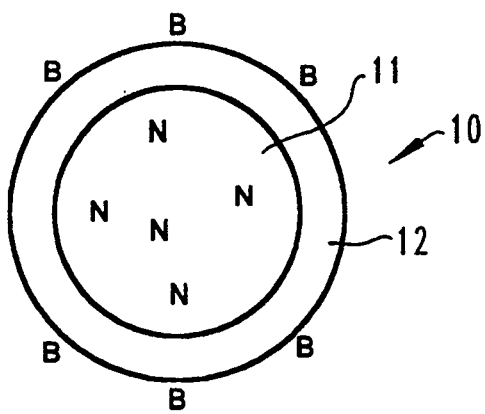
FIG. 1 is a schematic sectional view of a microcapsule of the present invention.

As used in the present invention the term "microcapsule" means both "true" microcapsules and microspheres. True microcapsules are those having a core surrounded by a distinct coating. Microspheres are microcapsules in which the core material is dispersed throughout a coating material. These two types of microcapsules are shown in the drawings.

With respect to the microorganisms that can be utilized in the present invention, any having the capability of degrading a hydrocarbon can be utilized, a number of which are known in this art, such as a bacterium from the genus Pseudomonas containing plasmids for providing hydrocarbon degradative pathways and bacterium from the genus Vibrio, Micrococcus, Bacillus, Arthrobacter, Nocardia, and Corynebacterium.

It is also within the scope of the present invention to include two different organisms capable of degrading hydrocarbons in the same capsule and in those instances where the byproducts of hydrycarbon degradation may themselves be undesirable in the environment, to include with the hydrocarbon-degrading organism, an organism capable of degrading the undesired byproduct to an environmentally-acceptable product.

A critical feature of the instant invention is the incorporation with the microorganism chosen of the nutrient or nutrients that are necessary to ensure the continued sustenance and viability of the organism. The nutrient(s) necessary for any given microorganism are well-known and those that are to be included in the microcapsules are those known to be suitable for that particular organism. Since such nutrients are seldom present in the areas where spills occur this ensures the viability of the organisms in that environment in order to enable them to live and reproduce at levels sufficient to degrade the hydrocarbon.

It is essential in making the microcapsules that the nutrients be in close proximity to the bacteria so that they can be readily utilized to maintain the viability and growth of the microorganisms as they are attacking and degrading the hydrocarbon.

The nutrients are placed in a lipophilic carrier prior to being encapsulated or dispersed in the coating material in forming the microcapsules in order that they may be released on a sustained basis for use by the organisms and also so that they cannot be leached away from the microorganisms by water in those situations in which the capsules are applied to a spill on water. The lipophilic materials used for this purpose include any conventional material for forming microcapsules which are not toxic for the organism such as waxes, glycerides and biodegradable materials such as polycaprolactone. The particular carrier material can be selected for any given microorganism by routine experimentation.

In the case of the "true" microcapsuLe in which the core material, usually a single core, is surrounded by a distinct coating, the nutrient materials are first dispersed in the lipophilic material and the coating is applied thereover to form microcapsules utilizing any of the conventional microcapsule forming procedures well-known to those in the microcapsules forming art. It is preferred to use the procedures set forth in U.S. Pat, Nos. 3,310,612; 3,015,128; 4,675,140; and 4,764,317 to form the microcapsules and microspheres. The size of the microcapsules can vary widely from 10 to 5,000 microns or larger dependent upon a number of factors including the density desired.

The particular coating material utilized in forming the microcapsule should be water-insoluble. Suitable materials for this purpose are both natural and synthetic materials such as alginates, caseinares, polypectates insolubilized gelatin, methylcellulose, hydroxypropylmethyl cellulose, insolubilized starches, insolubilized hydrocolloids, such as gellan gum, or mixtures thereof. With certain of these materials, such as the alginates, it is known that a catalyst material such as a calcium salt is required in order to harden and insolubilize the same.

The microorganism utilized to degrade the hydrocarbon is preferably attached to the surface of or included within the capsule coating and, therefore, for such usage one must use a coating material on which the organism can attach itself or be included, such as the alginate which is a preferred coating material.

A suitable manner of forming the microcapsule is to prepare the lipophilic dispersion or the core and to then coat it in the conventional manner with the alginate, as noted above, to form the microcapsules and then to apply the microorganism to the outer surface layer the capsules, namely on the surface of the alginate coating. The microorganism is preferably in the form of a bacterial suspension and can be included in the coating formulation itself before the microcapsules are formed and the organisms will extend throughout the coating layer.

Referring to the drawings FIG. 1 shows capsule 10 having core 11 containing dispersed therein the nutrients N. The core is surrounded by coating 12 containing on its outer surface the microorganisms B.

Figure 2:
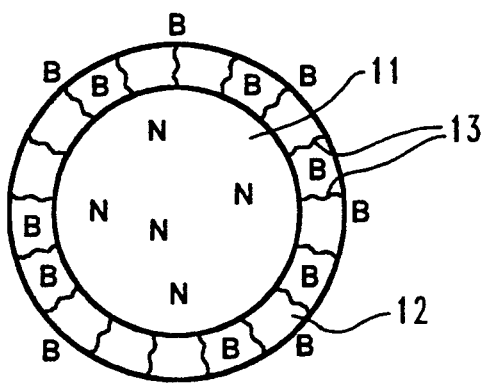
FIG. 2 is a schematic sectional view of an alternate embodiment of a microcapsule of the present invention.

In an alternate embodiment the microcapsule shown in FIG. 2, in which the same elements are present, there are in addition fissures 13 in coating 12 so that the microorganisms can be attached on the surface coating 12 and in fissures 13. The fissures can be created in the coating by adding to the coating material a solvent extractable material and dissolving such material away after the microcapsules are formed and prior to the addition of the microorganisms. One typical way of doing this is by the addition of water-soluble starches with the alginate coating. The fissures are desired since a larger quantity of bacteria can be attached to the capsules since the fissures increase the available surface area. In addition, the fissures will increase the diffusion of food (hydrocarbon), oxygen, nutrients, and the products and byproducts of degradation of the food to and from the encapsulated microorganism.

Figure 3:
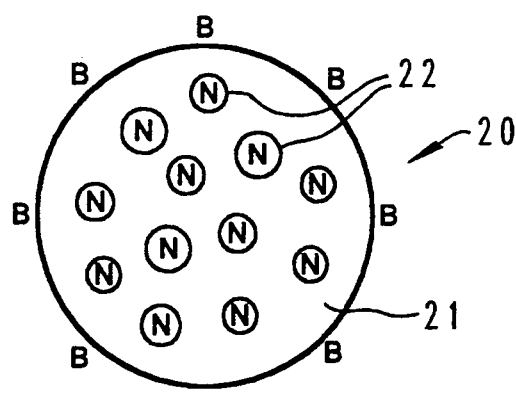
FIG. 3 is a schematic sectional view of a microsphere of the present invention.
Figure 4:
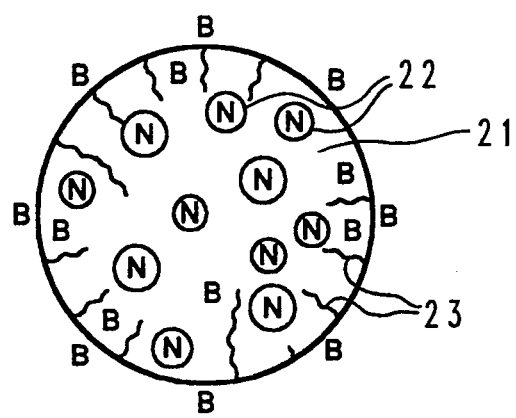
FIG. 4 is a schematic section view of an alternate embodiment of a microsphere of the present invention.

In the microsphere type of microcapsule wherein the core material is dispersed throughout a coating material, again the nutrients are dispersed in the lipophilic material and the resulting mixture is suspended as droplets in a solution of the coating material prior to forming the microsphere. This type of microcapsule 20 is shown in FIG. 3 in which matrix 21 surrounds a number of different size droplets 22 containing the nutrient material N. The bacteria B is applied in the same manner as in making the microcapsules, and here again the fissures 23 can be created in the coating material in the same manner as for the microcapsules. This is illustrated in FIG. 4.

An advantage of the instant invention is the fact that the microcapsules can be freeze-dried. This technique of freeze-drying or lyophilization is conventional in treatment of microorganisms and is a technique for maintaining their viability for long periods of time. The advantage herein is that the microcapsules can be lyophilized and maintained in that condition until time for usage, permitting the manufacture of large quantities for storage. They then can simply be applied in that form when the oil spill is on an aqueous environment such as ocean or river and the water present in that environment will quickly activate the lyophilized microcapsule permitting the microorganism to then exercise its hydrocarbon degrading activity. In situations where the oil spill is on a land surface, the lyophilizied microorganism can simply be mixed with an aqueous material, such as water, and they will activate and they then can be sprayed onto the hydrocarbon desired to be degraded. The capsules can also be used on beaches by controlling the density in order to mix with sand and/or dirt in surf areas to reach oil globules in sand and/or dirt.

Of importance in the instant invention is the ability to control the density of microcapsules by the amount of lipophilic material utilized or by the addition of low-density inert fillers and the size of the microcapsules and/or the surface chemistry thereof by the use of surfactants, such as TWEENS, SPANS, and mixtures thereof in the coating. This allows positioning of the micro-capsules at the desired location in the spill. That is to say, for example, in spills on a water area such as a river, the microcapules can be positioned to be near the oil-water interface. The density will keep the microcapsules in close proximity to the oil and with the nutrients present to allow for their growth and reproduction, the organisms are capable of then effectively degrading the hydrocarbon. A further advantage of the instant invention is that by having the nutrients and the microorganism, such as a bacterium, in one solid body, the dilution of the bacterium and/or nutrients within the large body, for example, water is drastically diminished and the microorganisms survive for longer periods of time and can be more effective in the degree of hydrocarbon degradation that they can effect.

The invention will be further discussed in connection with the following example which is set forth for purposes of illustration only.

EXAMPLE

Microcapsules are formed utilizing polycaprolactone as the lipophilic material and calcium alginate as the outer coating. The microorganism utilized is a bacterium from the genus Pseudomonas containing therein at least two stable energy-generating plasmids, each of the plasmids providing a separate hydrocarbon-degradative pathway. The nutrients utilized are those required by said organism for sustenance.

The nutrients are first dispersed in the polycaprolactone and then the microcapsules are formed by coating spheres of the lypophilic material containing the nutrients with the alginate. Once the microcapsules are formed a suspension of the microorganisms is applied to the surface of the microcapsules and the microcapsules are then lyophilized.

When needed for use the microcapsules are activated by being placed in water.

While discussion has been had above with respect to oil spills, it will be evident the instant invention is applicable to other hydrocarbon chemical spills, toxic land fills, and the like kinds of hydrocarbon contamination.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A microcapsule for use in degrading a hydrocarbon consisting essentially of, a coating material, and at least one microorganism capable of degrading said hydrocarbon, said core material comprising a lipophilic material containing nutrients necessary for the sustenance of said microorganism, said coating material being water-insoluble, and said capsule having a density and/or surface chemistry such that said microcapsule is kept at the oil-water interface in close proximity to said hydrocarbon to be degraded when said microcapsule is applied thereto, said at least one microorganism being on the outer surface of said coating, included in said coating, or both.

2. The microcapsule of claim 1 wherein said microcapsule comprises a core of said lipophilic material having said nutrients dispersed substantially uniformly therethrough completely coated with said coating.

3. The microcapsule of claim 1 wherein said microcapsule comprises a coating material having dispersed therein droplets of said lipophilic material having said nutrients dispersed substantially uniformly therethrough said droplets, said at least one microorganism being on the outer surface of said microcapsule, included in said coating material, or both.

4. The microcapsule of claim 1, 2, or 3 wherein said core material is a polycaprolactone and said coating material is an alginate.

5. The microcapsule of claim 1, 2, or 3 wherein the microcapsule is lyophilized.

6. The microcapsule of claim 1, 2, or 3 wherein two or more different microorganisms capable of degrading said hydrocarbon are included with said microcapsule.

7. A method of degrading a hydrocarbon comprising applying to said hydrocarbon a microcapsule or microcapsule system of any one of claims 1 to 3.

8. A method of claim 7 wherein the microcapsule or microcapsule system is formed into a slurry in a liquid and then applied by spraying onto the said hydrocarbon.

9. The method of claim 7 wherein said hydrocarbon is an oil slick on a body of water and said microcapsule or microcapsule system is applied thereon in a lyophilized condition.

10. The method of claim 9 wherein the density or surface chemistry of said microcapsule or microcapsule system is such as to cause the microcapsule or microcapsule system to stay on the surface of said hydrocarbon.

11. The method of claim 7 wherein the density or surface chemistry of said microcapsule or microcapsule system is such as to cause the microcapsule or microcapsule system to be positioned near the oil-water interface.

* * * * *

UNITED STATES PATENT AND TRADEMARK OFFICE
CERTIFICATE OF CORRECTION

PATENT NO : 5,348,803
DATED : September 20, 1994
INVENTOR(S) : Herman W. Schlameus, et. al.

It is certified that error appears in the above-identified patent and that said Letters Patent is hereby corrected as shown below:

Title page, item [75], inventor: should read -- Schlameus--.

Signed and Sealed this

Sixteenth Day of May, 1995

*Attest:*

BRUCE LEHMAN

*Attesting Officer*     Commissioner of Patents and Trademarks